United States Patent [19]

Heine et al.

[11] Patent Number: 5,333,018

[45] Date of Patent: Jul. 26, 1994

[54] BINOCULAR OPHTHALMOSCOPE

[75] Inventors: Helmut A. Heine; Otto H. Schmidt, both of Herrsching; Helmut Rosenbusch, Welthelm, all of Fed. Rep. of Germany

[73] Assignees: Heine Optotechnik GmbH, Herrsching, Fed. Rep. of Germany; Propper Manufacturing Co., Inc., Long Island City, N.Y.

[21] Appl. No.: 20,178

[22] Filed: Feb. 22, 1993

Related U.S. Application Data

[63] Continuation of Ser. No. 637,909, Jan. 7, 1991, abandoned.

[51] Int. Cl.⁵ .............................................. A61B 3/10
[52] U.S. Cl. .................................. 351/221; 351/205; 359/377
[58] Field of Search ............. 351/205, 206, 207, 208, 351/214, 221; 359/376, 377

[56] References Cited

U.S. PATENT DOCUMENTS

| | | | |
|---|---|---|---|
| 4,449,797 | 5/1984 | Kocher et al. | 351/205 |
| 4,681,413 | 7/1987 | Schmidt et al. | 351/205 |
| 4,684,227 | 8/1987 | Schmidt et al. | 351/205 |
| 4,699,481 | 10/1987 | Matsumura | 351/205 |

FOREIGN PATENT DOCUMENTS 3627251 2/1988 Fed. Rep. of Germany .
318487 4/1930 United Kingdom .

*Primary Examiner*—William L. Sikes
*Assistant Examiner*—Hung Xuan Dang
*Attorney, Agent, or Firm*—Oppedahl & Larson

[57] ABSTRACT

A stereoscopic ophthalmoscope for examining an eye including two inner reflection mirrors for guiding light representing the image of the eye toward a pair of external mirrors. Each of the external mirrors serves as an image splitter for dividing the light into two distinct optical observation paths. The first optical observation path is used to produce a stereoscopic image of the eye suitable for binocular viewing. The second optical observation path is used to produce a non-stereoscopic image of the eye suitable for monocular or binocular viewing.

12 Claims, 3 Drawing Sheets

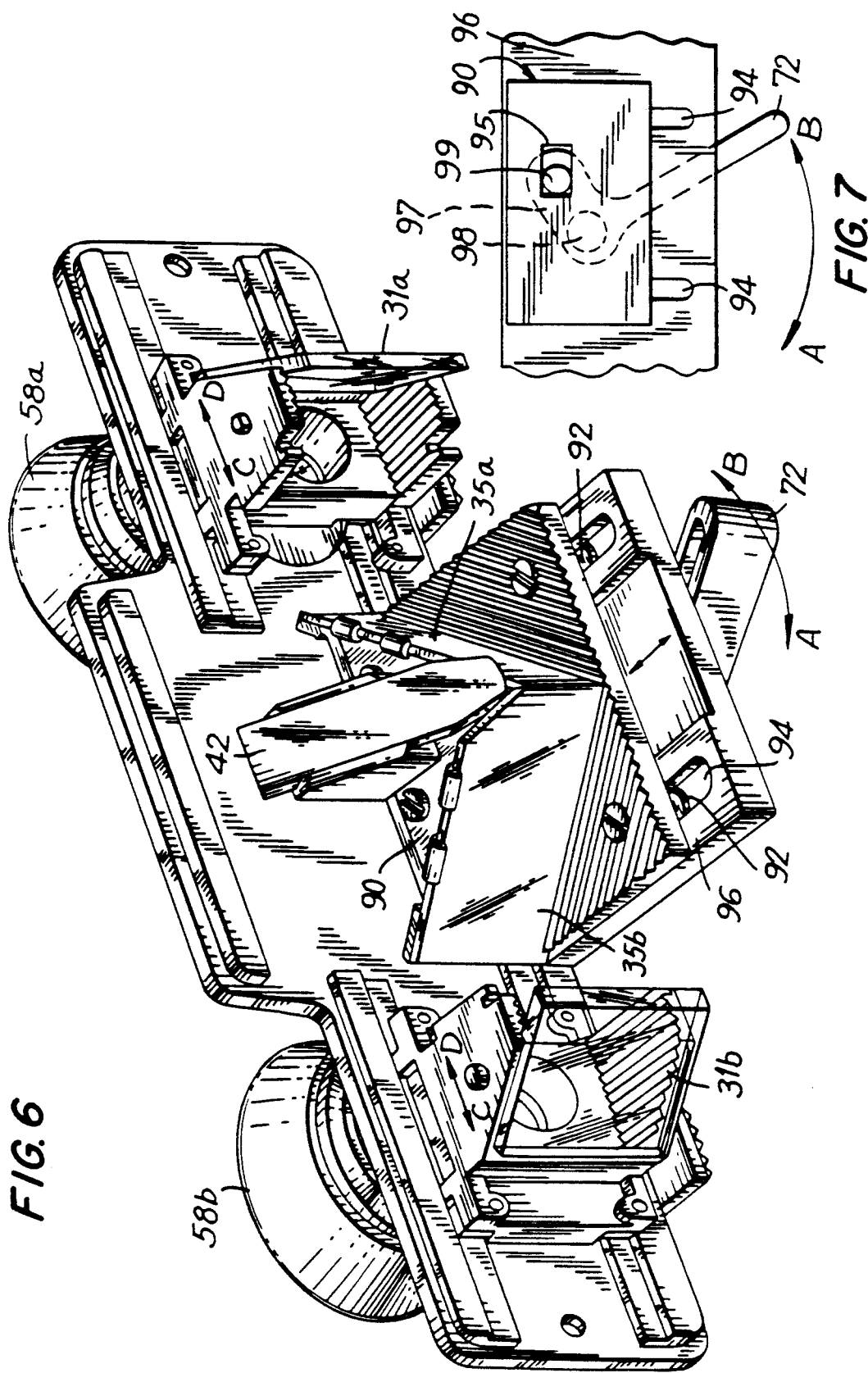

BINOCULAR OPHTHALMOSCOPE

This is a continuation of application Ser. No. 07/637,909 filed Jan. 7, 1991 now abandoned.

BACKGROUND OF THE INVENTION

This invention relates generally to a binocular stereoscopic viewing device, and in particular, to a binocular ophthalmoscope for stereoscopic observation of the fundus of the eye by more than one observer.

During ophthalmoscopic examinations, the images representing the examiner's pupils and an observation light source are directed to the pupil of the eye to be examined. For optimum stereopsis, the images representing the examiner's pupils must be separated from each other as far as possible while falling within the pupil of the eye to be examined. The image representing the light source, which must also strike the pupil of the eye to be examined, should be separated as far as possible from the images representing the examiner's pupils.

Preferably, the images representing the light source and the examiner's pupils are separated as far as possible from each other within each eye to be examined by dilating each pupil to be examined through the application of a drug. Dilation of a patient's eye at times may not be possible or practical. To stereoscopically view the patient's pupil when dilation of the latter is not practical or possible, binocular ophthalmoscopy is employed.

One type of conventional binocular ophthalmoscope is disclosed in U.S. Pat. No. 4,684,227, the internal mirror array structure of an ophthalmoscope 100 being shown in FIG. 1. More particularly, this first type of conventional binocular ophthalmoscope includes a pair of internal mirrors 15 and a pair of external mirrors 16. Internal mirrors 15 and external mirrors 16 redirect and separate a pair of light rays 12 and 13 representing the stereoscopic image from a portion (e.g. fundus) of a patient's eye 11. Prior to reflection by internal mirrors 15, light rays and 13 pass through an ophthalmoscopic lens 14, for redirecting light rays 12 and 13. Internal mirrors 15 and external mirrors 16, in combination, guide light rays 12 and 13 to the observer's eyes (not shown) through a pair of oculars 17.

In the German Patent No. DE 3627251, another type of conventional binocular ophthalmoscope is employed. In this binocular ophthalmoscope, the optical observation paths from the patient's eyes are redirected several times by a relatively complex mirror configuration incorporated within the housing of the device. A reduction in the quality of the image to be examined results.

For clinical and tutorial applications, it is often necessary for more than one observer (e.g. instructor and student) to participate in the examination of the patient's eye at the same time. Conventional multi-user binocular or monocular ophthalmoscopes for multi-user application are disclosed in British Patent Specification No. 318,487 and publications by the firm of Zeiss, Oberkochen of West Germany entitled "Ophthalmoscopy Equipment" Prospectus No. W 30-131-d (1976) and "Stereo Assistant Tube" Prospectus No. W 30-047-d (1974). The multi-user ophthalmoscope disclosed in these references includes so-called assistant viewing tubes which are attached to the housing of a binocular or monocular ophthalmoscope 200 shown in FIG. 2.

More particularly, as shown in FIG. 2, Light rays 12 and 13 representing the stereoscopic image from a portion of eye 11 a patient are redirected by ophthalmoscopic lens 14 prior to striking an image splitter 28. Those portions of light rays 12 and 13 reflected by image splitter 28 are redirected to the assistant viewing tubes (not shown) along optical observation paths 20 and 21. Light rays 12 and 13 also pass through image splitter 28, are reflected by a pair of internal mirrors 25 and then by a pair of external mirrors 26 to redirect light rays 12 and 13 through oculars (not shown) prior to reception by an observer's eyes to form a stereoscopic binocular image. Each of the assistant viewing tubes receives a monocular ophthalmoscope image based on either optical observation path 20 or 21.

The multi-user ophthalmoscope 200 of FIG. 2 although providing for more than one observation at the same time is difficult to handle and susceptible to breakage, scratches, dust and dirt on various glass surfaces. Frequent replacement on the glass surfaces results. The intensity of light rays 12 and 13 diminished by the loss of light through image splitters 28 redirecting light toward the assistant viewing tube. Scattered light from one or more external sources through the assistant viewing tubes also interferes with the examination of the patient's eye.

Accordingly, it is desirable to provide an improved multi-user binocular ophthalmoscope which is easier to handle and less susceptible to breakage, scratches, dust and dirt on various glass surfaces. The ophthalmoscope also should prevent scattered light from external sources from entering into the device and thereby avoid scattered light from interfering with examination of the patient's eye.

SUMMARY OF THE INVENTION

Generally speaking, in accordance with the invention, a binocular stereoscopic viewing device for examining an eye includes a light source for illuminating the eye; a first light guide for reflecting light representing the image of the eye; and second light guides for reflecting and transmitting the light produced by the first light guide. The light reflected by the second light guides represents a stereoscopic image of the eye suitable for binocular viewing. The light transmitted by the second Light guides represents a non-stereoscopic image of the eye suitable for monocular or binocular viewing.

In accordance with one feature of the invention, the second light guides are image splitters. In accordance with another feature of the invention, the first light guide includes a pair of mirrors.

By using image splitters as the second light guides, a multi-user binocular ophthalmoscope which is easier to handle and less susceptible to breakage, scratches, dust and dirt on various glass surfaces is provided. The binocular stereoscopic viewing device reduces the number of optical components required to provide multi-user application. A reduction in the cost, weight and size of the device as compared to conventional binocular ophthalmoscopes results. In particular, the disadvantages of assistant viewing tubes is avoided.

The second light guides are preferably detachable. The image splitters can therefore be replaced with non-transparent mirrors (i.e. reflect but do not transmit light).

Accordingly, it is an object of the invention to provide an improved binocular ophthalmoscope which is easier to handle.

It is another object of the invention is to provide a binocular ophthalmoscope which is less susceptible to breakage, scratches, dust and dirt on glass surfaces of the device.

It is still another object of the invention to provide a binocular ophthalmoscope which avoids scattered light from external sources being introduced into the device.

Still other objects and advantages of the invention will in part, be obvious and will, in part, be apparent from the specification.

The invention accordingly comprises several steps and the relation of one or more of such steps with respect to each of the other and the device embodying the features of construction, combination of elements, and arrangement of parts which are adapted to effect such steps, all are exemplified in the following detailed disclosure, and the scope of the invention will be indicated in the claims.

BRIEF DESCRIPTION OF THE DRAWINGS.

For a fuller understanding of the invention, reference is had to the following description taken in connection with the accompanying drawings, in which:

FIG. 6 is a perspective view of the observation unit of the binocular ophthalmoscope of FIG. 4; and FIG. 7 is a bottom plan view of the binocular ophthalmoscope.

DETAILED DESCRIPTION OF THE PREFERRED EMBODIMENTS

Figure 1:
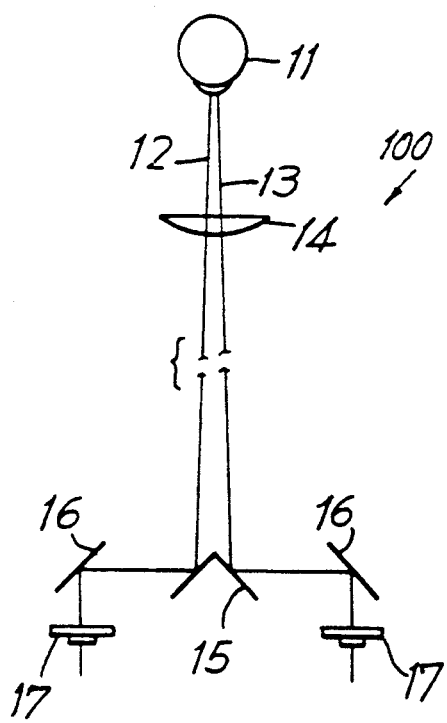
FIG. 1 is a schematic diagram of a first conventional binocular ophthalmoscope in accordance with the prior art.
Figure 2:
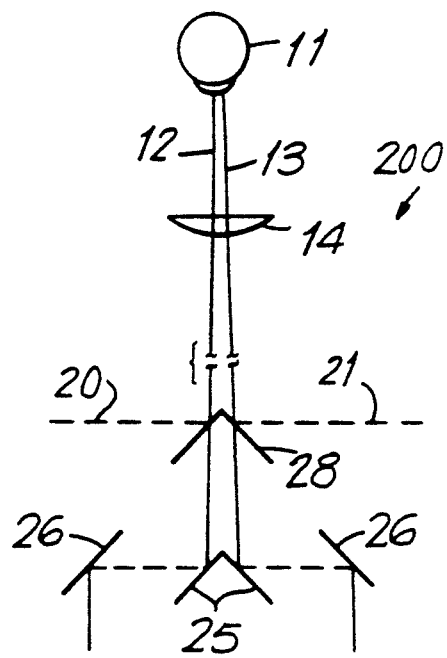
FIG. 2 is a schematic diagram of a second conventional binocular ophthalmoscope in accordance with the prior art.
Figure 3:
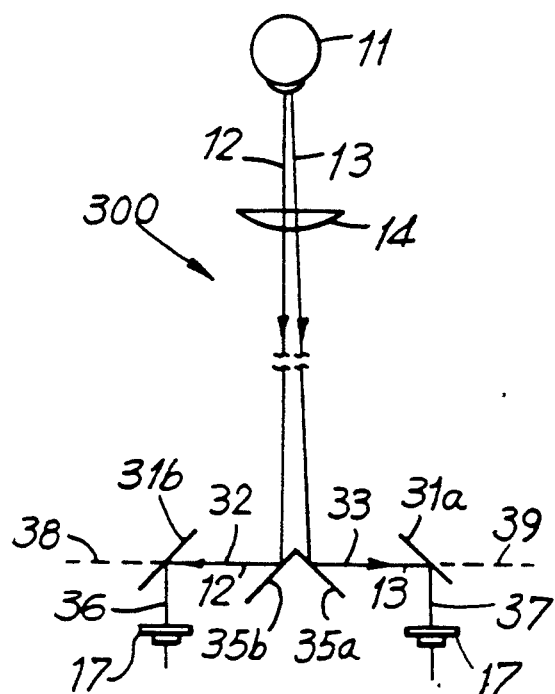
FIG. 3 is a schematic diagram of a binocular ophthalmoscope in accordance with the present invention.

Referring now to FIG. 3, a binocular ophthalmoscope, generally indicated at 300, and constructed in accordance with the preferred embodiment of the invention includes a pair of internal mirrors 35a and 35b for reflecting light rays 12 and 13, which are redirected by ophthalmoscopic lens 14 and represent the image from a portion (e.g. the fundus) of eye 11, similar to the binocular ophthalmoscope 100 of FIG. 1.

A pair of image splitters 31a and 31b receive the images reflected by internal mirrors 35a and 35b, respectively. Internal mirrors 35a and 35b redirect light rays 13 and 12 so as to travel in the same plane, but in opposite directions along optical observation paths 33 and 32, respectively.

Light rays 12 and 13 are further divided by image splitters 31a and 31b, respectively. Image splitter 31a creates a pair of optical observation paths 37 and 39 along which light ray 13 travels. Image splitter 31b creates a pair of optical observation paths 36 and 38 along which light may 12 travels. Light rays 12 and 13 travel along optical observation paths 36 and 37, respectively, and then through oculars 17 to the examiner's eye (not shown), to create a binocular stereoscopic vision of eye 11. At the same time, light rays 12 and 13 travel along optical observation paths 38 and 39, respectively, in creating a monocular or binocular non-stereoscopic image of eye 11.

The stereoscopic and non-stereoscopic images of eye 11 are produced by ophthalmoscope 300 without interference from other light sources. Further, by reducing the number of light guides required as compared to ophthalmoscope 200, ophthalmoscope 300 provides an image of eye 11 which is far less distorted. The loss of light from patient's eye 11 can be avoided by ophthalmoscope 300 by replacing image splitters 31a and 31b with external mirrors when third party viewing is not required.

Figure 4:
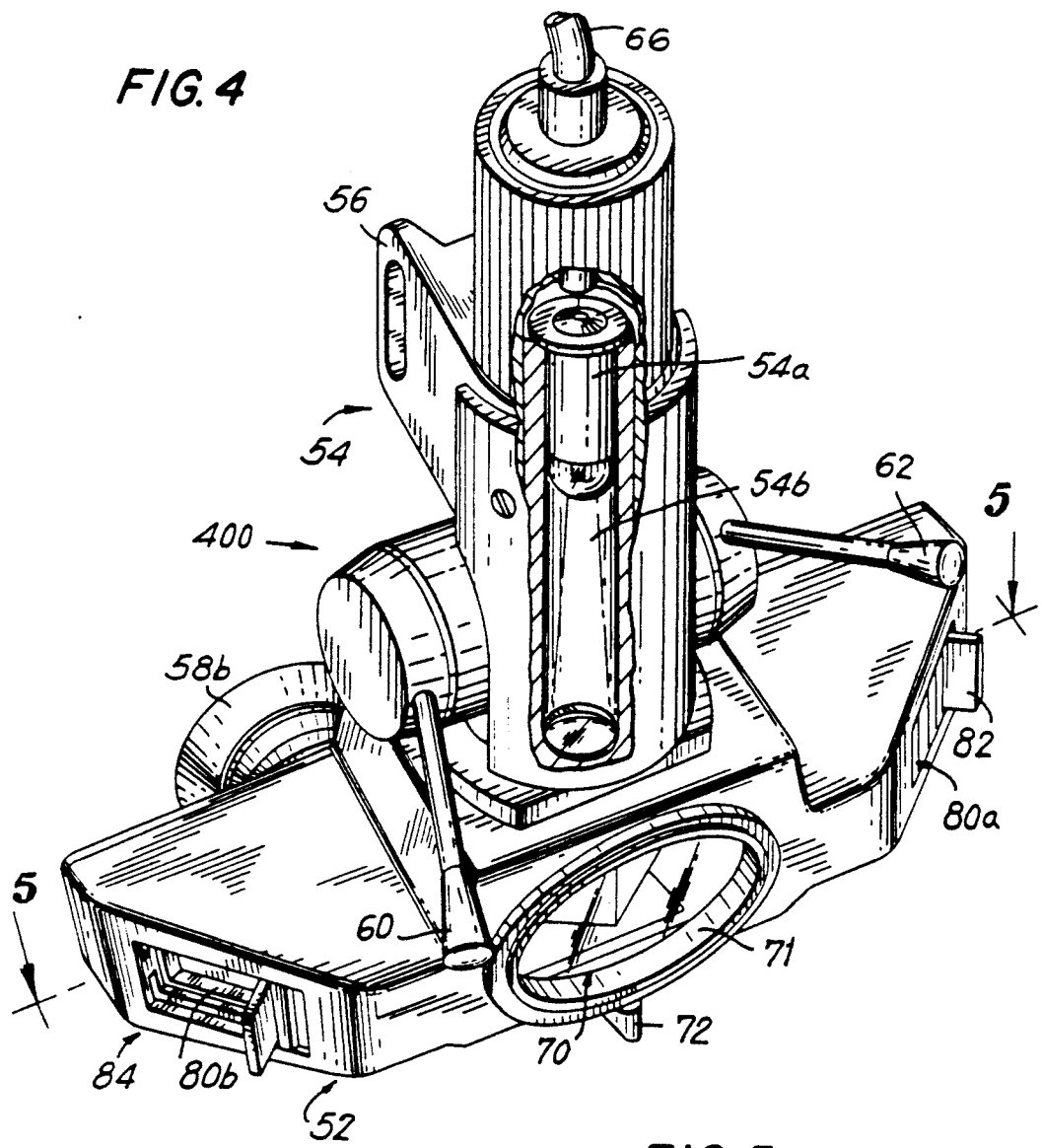
FIG. 4 is a perspective view of a binocular ophthalmoscope in accordance with the present invention.
Figure 5:
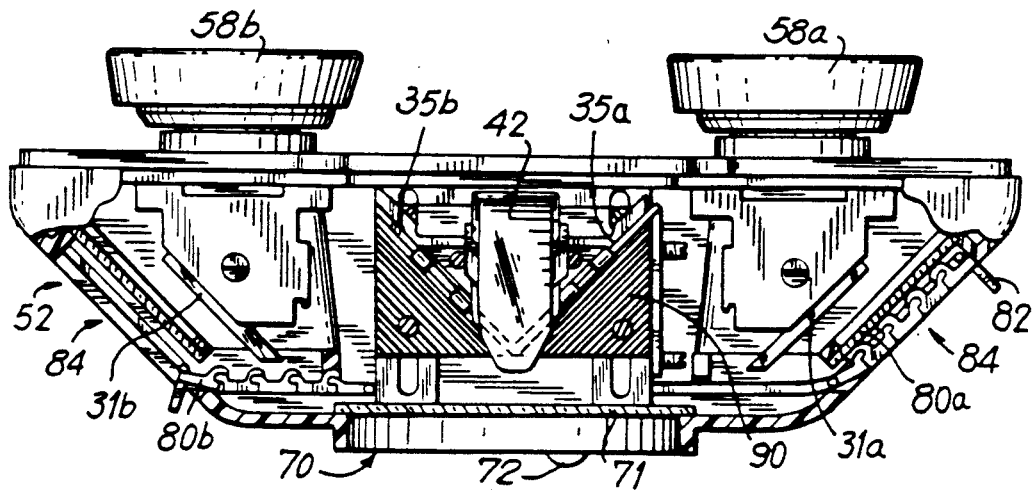
FIG. 5 is a sectional view along lines 5—5 of FIG.

FIGS. 4–6 illustrate a binocular ophthalmoscope 400 accordance with the invention incorporating the light guide array of FIG. 3. Many of the elements and construction of binocular ophthalmoscope 400 are similar to the binocular ophthalmoscope disclosed in U.S. Pat. No. 4,684,227 which is incorporated herein by reference thereto.

Binocular ophthalmoscope 400 includes an illumination unit 54 and an observation unit 52 rigidly connected thereto. A bracket 56 is secured to illumination unit 54 and can be used to fasten binocular ophthalmoscope 400 to a headband (not shown), or to a spectacle frame (not shown). Adjustable eyepieces 58a, 58b are secured to illumination unit 54 through which a user (examiner) observes pupil 11 of a patient. Eyepieces 58a and 58b can be moved in directions denoted by arrows C and D to adjust for the interpupillary distance of the observer. Levers 60 and 62 can be used to couple luminous-field diaphragms and filters into the math of illumination from illumination unit 54 to the patient. Illumination unit 54 includes a halogen lamp light source which is supplied with current through a cable 66. In an alternative embodiment, fiber optic illumination may be provided by means of an external light source and a fiber optics cable.

An optical aperture or window 70 through which light passes between the patient and the observer is closed by a plain glass disk 71 to prevent the intrusion of dust into observation unit 52. A single lever 72, which is centrally located relative to observation unit 52 and equally accessible to both left-handed and right-handed users, can be used to simultaneously set the position of the images of the examiner's pupil and the position of the image of the light source in pupil 11 of the patient, i.e., convergence and parallax.

A pair of windows 80a and 80b are provided in a pair of side portions 84 of binocular ophthalmoscope 400 to allow third parties to view the image represented by light rays 12 and 13, respectively. Windows 80a and 80b are each provided with a sliding door 82 to open and close the associated window.

In operation, the path of illumination from the light source within illumination unit 54 passes through (not shown) a condensing lens in a diaphragm (not shown) which can be adjusted by lever 60. Optical filters within illumination unit 54 can be placed in and removed from the illumination path by means of lever 62. An objective lens produces an image of the diaphragm at a defined distance in front of ophthalmoscope 400. A more detailed discussion of the illumination path is disclosed in U.S. Pat. No. 4,684,227 which has been incorporated herein by reference thereto. The optical axis of illumination is deflected by an illumination mirror 42 through aperture 70 in the direction of the eye 11 of the patient. Illumination mirror 42 is supported on a mirror carrier 90 towards and away from the patient's eye, changing the separation of the axis of illumination from the observation plane defined by light rays 12 and 13.

The directions of light rays 12 and 13 are redirected by internal mirrors 35b and 35a such that light rays travel in the same plane but in opposite directions with respect to one another along optical observation paths 32 and 33, respectively. The paths along which light rays 12 and 13 travel are further divided by image splitters 31b and 31a as discussed above.

Light rays 12 and 13 travel through image splitters and 31a and then along optical observation paths 38 and 39 before passing through windows 80a and 80b, respectively. When doors 82 of windows 80a and 80b are open, third party viewers may view the non-stereoscopic view of eye 11. A binocular view of the stereoscopic image of eye 11 is provided through oculars 17.

Referring now to FIGS. 6 and 7, a pair of mirrors 35a and 35b and illumination mirror 42 are mounted to mirror carrier 90. Mirror carrier 90 slidably rests on a plate 96 forming the interior bottom of the housing of observation unit 52. Mirror carrier 90 includes two rail shaped projections 92 which are disposed in and slidably engaged by two slot-shaped recesses 94 formed in plate 96 which together serve as a carriage-like guideway. Recesses 94 extend parallel to the observation plane and parallel to the axis of aperture 70 so that mirror carrier 90 is displaceably moved towards and away from aperture 70. Lever 72 is pivotally mounted to plate 96 through a pivot rotatably mounted to plate 96. The pivot includes a shaft 98 projecting through an opening in plate 96 outwardly from the bottom of observation unit 52, an arm 97 extending at an angle with lever 72 parallel to the bottom of observation unit 52 and a recess of plate 96 in a cam guide 99 received in a cam recess 95 in the bottom of mirror carrier 90. Lever 72 is secured to shaft 98 so that the pivoting of lever 72 rotates shaft 98. Accordingly, cam guide 99 moves mirror carrier 90 as cam guide 99 slides in cam recess 95. Lever 72 pivots in the directions of arrows A and B thereby displacing mirror carrier along slot-shaped recesses 94 towards and away from aperture 70, respectively.

As now can be readily appreciated, ophthalmoscope 400 according to the invention enables a third party to view eye 11 of a patient through windows 80a and 80b of observation unit 52. By closing one or both doors 82, when windows 80a and/or window 80b are not in use, the amount of glare and other outside influences in the system which interface with the image being examined can be reduced further. In an alternative embodiment, fiber optic bundles (i.e., image conductor bundle) can be coupled to windows 80a and 80b to provide the image of the patient's eye (e.g. retina) to a larger display screen.

Accordingly, binocular ophthalmoscope 300, 400 reduces the cost, weight and size of conventional ophthalmoscope 200 by omitting at least two light guide components, their carriers and attachments. In addition, scattered light from outside sources decreased since assistant viewing tubes are eliminated.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A multi-user binocular stereoscopic viewing device for examining an eye, comprising:
   a housing:
   light source means for supplying light to illuminate the eye and positioned in said housing;
   first light guide means for reflecting light supplied by said light source means and representing the image of the eye, said first light guide means positioned in said housing;
   second light guide means for reflecting and transmitting said light produced by said first light guide means, said second light guide means positioned in said housing
   binocular viewing means positioned on said housing for receiving said light reflected by said second light guide means, said reflected light representing a stereoscopic image of the eye suitable for binocular viewing by a first user through the binocular viewing means, and
   window means positioned on said housing for receiving said light transmitted by said second light guide means, said transmitted light representing a non-stereoscopic image of the eye suitable for viewing by at least a second user through the window means.

2. The binocular stereoscopic viewing device of claim 1; wherein the second light guide means includes image splitters.

3. The binocular stereoscopic viewing device of claim 2; wherein the first light guide means includes mirrors.

4. The binocular stereoscopic viewing device of claim 3, wherein the second light guide means is replaceable with a mirror means for reflecting said light produced by said first light guide means.

5. The binocular stereoscopic viewing device of claim 2, wherein the second light guide means is replaceable with a mirror means for reflecting said light produced by said first light guide means.

6. The binocular stereoscopic viewing device of claim 1; wherein the first light guide means includes mirrors.

7. The binocular stereoscopic viewing device of claim 6, wherein the second light guide means is replaceable with a mirror means for reflecting said light produced by said first light guide means.

8. The binocular stereoscopic viewing device of claim 1, wherein the second light guide means is replaceable with a mirror means for reflecting said light produced by said first light guide means.

9. A method for multi-user observation of an eye through a binocular ophthalmoscope, the binocular ophthalmoscope having a binocular viewing station and a window viewing station comprising the steps of:
   illuminating the eye;
   reflecting light representing an image of the eye by a first light guide means;
   reflecting and transmitting said light by a second light guide means;
   viewing said light reflected by said second light guide means represented by a stereoscopic image of the eye suitable for binocular viewing by a first user through the binocular viewing station; and
   viewing said light transmitted by said second light guide means represented by a non-stereoscopic image of the eye by at least a second user through the window viewing station.

10. The method of a claim 9; wherein the step of reflecting and transmitting said light includes splitting the image of the eye through use of an image splitter.

11. The method of claim 9; wherein the step of reflecting light by said first light guide means includes redirecting the light toward said second light guide means.

12. The method of claim 10; wherein the step of reflecting light by said first light guide means includes redirecting the light toward said second light guide means.

* * * * *